(12) United States Patent
Hovanesian

(10) Patent No.: US 7,780,653 B2
(45) Date of Patent: Aug. 24, 2010

(54) METHODS AND APPARATUS FOR VISION CORRECTION

(76) Inventor: John A. Hovanesian, 980 Wilson St., Laguna Beach, CA (US) 92651

(\*) Notice: Subject to any disclaimer, the term of this patent is extended or adjusted under 35 U.S.C. 154(b) by 1022 days.

(21) Appl. No.: 11/232,457

(22) Filed: Sep. 20, 2005

(65) Prior Publication Data

US 2006/0155264 A1    Jul. 13, 2006

Related U.S. Application Data

(60) Provisional application No. 60/611,650, filed on Sep. 20, 2004.

(51) Int. Cl.
*A61B 18/18* (2006.01)
(52) U.S. Cl. .......................... 606/4; 128/898
(58) Field of Classification Search ................ 606/4–6, 606/107, 166; 128/898
See application file for complete search history.

(56) References Cited

U.S. PATENT DOCUMENTS

| | | | | |
|---|---|---|---|---|
| 4,646,720 A * | 3/1987 | Peyman et al. | ............... | 128/897 |
| 4,840,175 A * | 6/1989 | Peyman | ......................... | 606/5 |
| 5,152,759 A * | 10/1992 | Parel et al. | ...................... | 606/5 |
| 5,549,632 A | 8/1996 | Lai | ............................... | 606/5 |
| 5,713,967 A | 2/1998 | Hamerlinski | ................. | 44/630 |
| 5,964,748 A * | 10/1999 | Peyman | ......................... | 606/5 |
| 6,361,560 B1 | 3/2002 | Nigam | ....................... | 623/5.14 |
| 6,454,800 B2 | 9/2002 | Dalton | ....................... | 623/5.11 |
| 6,607,566 B1 | 8/2003 | Coleman et al. | ............... | 44/301 |
| 6,623,522 B2 | 9/2003 | Nigam | ....................... | 623/5.13 |
| 6,689,165 B2 | 2/2004 | Jacob et al. | ................. | 623/5.16 |
| 6,702,807 B2 | 3/2004 | Peyman | ........................ | 606/5 |
| 6,893,461 B2 | 5/2005 | Nigam | ....................... | 623/5.11 |
| 6,918,904 B1 * | 7/2005 | Peyman | ......................... | 606/5 |
| 7,001,374 B2 * | 2/2006 | Peyman | ......................... | 606/5 |
| 2005/0090895 A1 * | 4/2005 | Peyman | ..................... | 623/5.11 |
| 2006/0064077 A1 * | 3/2006 | Peyman | ......................... | 606/5 |

OTHER PUBLICATIONS

Hovanesian et al., Induced Astigmatism Following Laser in situ Keratomileusis for Myopia With a Free Cap, 2000, Journal of Refractive Surgery, 16, 375-379.*

(Continued)

*Primary Examiner*—Henry M Johnson, III
*Assistant Examiner*—Aisha Hunte
(74) *Attorney, Agent, or Firm*—Robert D. Buyan; Stout, Uxa, Buyan & Mullins

(57) ABSTRACT

Methods and apparatus/articles of manufacture for improving or correcting vision in an eye of a human or animal subject. A quantity of corneal tissue is removed from the subject's eye. Thereafter, a corneal cap is affixed to the anterior surface of the subject's eye in place of the previously removed corneal tissue. The shape and/or thickness and/or rotational orientation of the affixed corneal cap is adjusted as needed such that vision through the subject's eye is improved or corrected. In some cases, the corneal cap may comprise the same corneal tissue that was initially removed from the subject's eye. In other cases, the corneal cap may be formed of corneal tissue that has been harvested from a donor eye (e.g., a human, animal or cadaveric donor) or other material (e.g., synthetic or polymer material) having suitable properties.

4 Claims, 5 Drawing Sheets

OTHER PUBLICATIONS

Mortada, Aly, Rectangular Autoenous Lamellar Keratoplasty, 1963, Brit. J. Opththal., 47, 232-236.*

Tanure et al., Ceratoplastia penetrante autóloga ipsilateral com rotação do disco corneano em casos de ceratocone—resultados iniciais / Autologous ipsilateral rotating penetrating keratoplasty for keratoconus: a preliminary report, Rev. Bras. Oftalmol, 2001, 60(10), 719-729.*

* cited by examiner depth (mm) ≈ diameter ² (mm) X diopters / 3

Munnerlyn Formula:  depth (mm) ≈ diameter $^2$ (mm) X diopters / 3

Modified:         e − c ≈ d2 x diop cyl / 6

Rearranging:      diop cyl ≈ 3 x (e − c) / d2

Assuming 90°     total correc ≈ 6 x (e − c) / d2

---

If a cylinder with power $d$ is rotated $\theta$ degrees, the magnitude of induced cylinder is
magnitude = cyl (2−2 cos 2θ)^ (1/2)

Magnitude reaches a maximum when θ = 90°

METHODS AND APPARATUS FOR VISION CORRECTION

RELATED APPLICATION

This application claims priority to U.S. Provisional Patent Application No. 60/611,650 filed on Sep. 20, 2004, the entirety of which is expressly incorporated herein by reference.

FILED OF THE INVENTION

This invention relates generally to the fields of medicine and surgery and more particularly to methods, apparatus and articles of manufacture useable for refractive vision correction in human or animal subjects.

BACKGROUND

The present invention generally relates to ophthalmic procedures and more specifically relates to methods for vision correction.

Refractive errors occur when light rays entering the eye are not focused precisely on the retina. In nearsightedness (myopia), light is focused in front of the retina. In farsightedness (hyperopia), light is focused behind the retina. In astigmatism, light is focused in more than one focal point.

Most people with astigmatism have "regular" astigmatism. Regular astigmatism usually occurs when the cornea (the front surface of the eye) has an oval (or toric) curvature rather than round curvature. In other words, one dimension (meridian) of the cornea is steep, and one dimension is flat.

"Irregular" astigmatism and "higher order aberrations" occur when the eye's focusing elements are neither round nor uniformly oval but irregular in their curvature. For example, the eye of a person with a thickened scar on one side of the cornea would have irregular focusing properties.

Conventional vision correction for astigmatism includes toric spectacles, soft contact lenses and rigid contact lenses. Rigid contact lenses are known to work well for many types of refractive error, including irregular astigmatism. Corrective lenses, however, are cumbersome, uncomfortable, and may present certain risks to the health of the cornea.

Conventional surgical vision correction includes radial or astigmatic keratotomy which involves deep incisions into the cornea to correct vision. These techniques have limitations in accuracy and in the magnitude of correction that can be achieved. Additionally, the incisions may mechanically weaken the cornea, compromise the structural integrity thereof, and cause the cornea to be more susceptible to injury, particularly in the case of a patient with a relatively large pupil size.

Excimer laser vision correction procedures (photorefractive keratectomy and lasik) require the use of expensive equipment and involve the permanent removal of corneal tissue, which can lead to corneal weakening. In lasik procedures, surgeons create a thin (130-160 micron) hinged "flap" of corneal tissue that is moved from the center of the cornea to expose its inner layers. Laser treatment is applied to the inner corneal layers in order to reshape the curvature. The corneal flap is then replaced in its original position and allowed to heal. During the surgical procedure, the flap is designed to remain attached to the cornea by its hinge.

The prior art has also included various corneal implants and other implants for vision correction, including but not limited to those described in U.S. Pat. Nos. 6,893,461; 6,702, 807; 6,623,522; 6,607,566 and 6,361,560, each of which is expressly incorporated herein by reference. Additionally, the prior art has included various corneal "onlays" which promote overgrowth of corneal epithelium, including but not limited to those described in U.S. Pat. Nos. 6,689,165; 6,454, 800 and 5,713,967, each of which is expressly incorporated herein by reference.

SUMMARY OF THE INVENTION

The present invention provides a method for improving or correcting vision in a human or animal subject. In general, this method comprises the steps of a) removing a quantity of corneal tissue from an eye of the subject and b) repositioning on the eye all or a portion of the removed corneal tissue (e.g., a corneal cap) such that the subject's vision through that eye will be better than it was prior to the performance of Step a. In at least some cases, the corneal tissue removed in Step a may have a shape and/or thickness that is selected based on a refractive error of the eye. Also, in at least some cases, the topography of the eye may be measured prior to performance of Step A and Step B may comprise repositioning at least a portion of the removed corneal tissue (e.g., a corneal cap) on the eye in a degree of rotation that is selected based on the previously acquired topographic measurement.

Further in accordance with the invention, there are provided corneal caps that may be grafted or affixed to the eye of a human or animal subject to improve or correct the subject's vision. Such corneal caps are generally made by a method comprising the steps of a) providing corneal tissue or material that mimics corneal tissue and b) modifying the shape and/or thickness of the tissue or material provided in step A as needed to form a corneal cap that, when affixed to the anterior surface of said subject's eye in a selected rotational orientation, will correct or improve vision in the subject's eye. In some cases, the corneal cap may be formed of the same corneal tissue that was initially removed from the subject's eye. In such cases, modifying the shape and/or thickness of the corneal cap may or may not be necessary but typically the removed corneal cap will be reaffixed to the eye in a rotational orientation that differs from its original rotational orientation. In other cases, the corneal cap may be formed of corneal tissue that has been harvested from a donor eye (e.g., a human, animal or cadaveric donor) or other material (e.g., synthetic or polymer material) having suitable properties and sized to fit on the area from which the corneal tissue was previously removed. Examples of synthetic polymers of which the corneal cap may be made include those previously used for corneal implants and corneal onlays as described in the United States Patents referred to above and incorporated herein by reference. The rotational orientation in which the corneal cap is affixed to the anterior surface of the eye may be selected to correct or improve vision based on a previously taken topographic measurement of the eye.

Further aspects, elements and details of the present invention will be understood upon reading the detailed description and examples set forth herebelow.

DETAILED DESCRIPTION AND EXAMPLES

Figure 1:
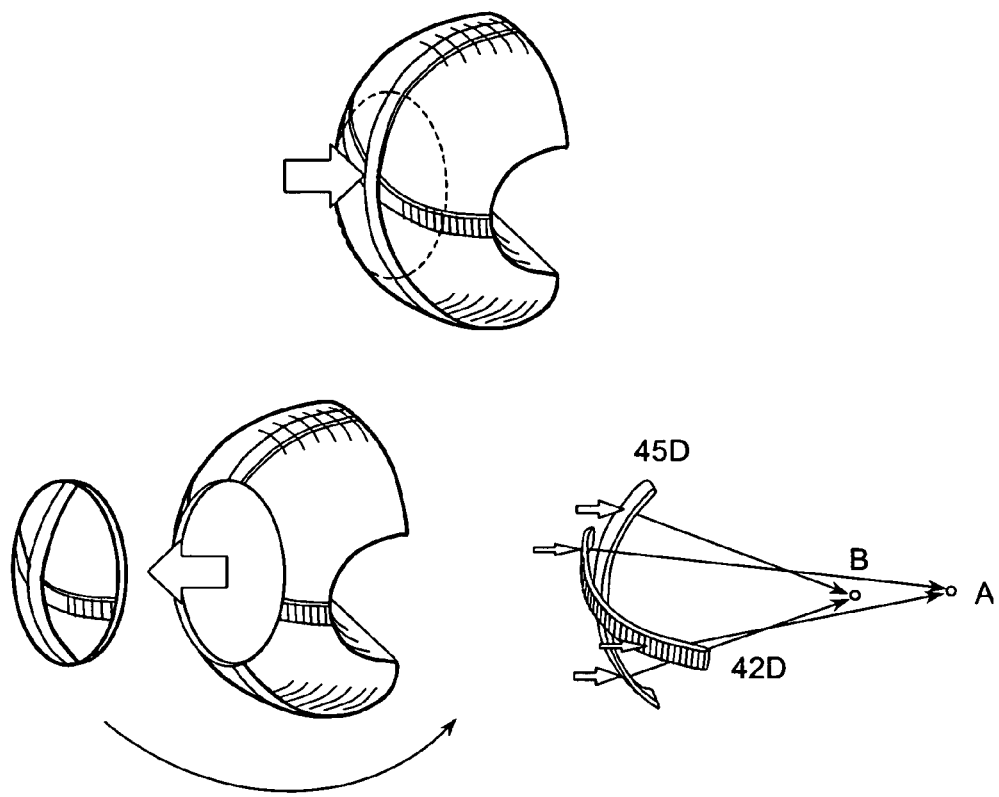
FIG. 1 shows a simplified representation of a surface of an eye that has regular astigmatism.

The present invention provides new methods of vision correction. The present methods are effective to at least minimize visual disability resulting from irregular focusing properties of the eye. The present methods are able to improve vision, for example, correct vision.

More specifically, the present methods are designed to be precise in achieving one or more desired vision corrections, for example, the present methods are suitable for correcting both large and small degrees of astigmatism, as well as higher order aberrations. In some embodiments of the present invention, methods are provided which are designed to be effective in improving or correcting vision in patients that may not be good candidates for conventional vision correction procedures, for example, but not limited to, those patients having relatively large pupils. The present invention provides methods that are effective in improving or correcting vision without compromising the strength and/or structure of the cornea. The present methods may allow a relatively shorter recovery time than conventional ophthalmic surgical procedures and, in some circumstances, are reversible.

Generally, the present invention provides methods for improving or correcting vision by adjusting a shape of a patient's cornea. More particularly, the present invention provides for repositioning a portion of corneal tissue of an eye, for example an astigmatic eye, by removing a portion of corneal tissue, for example, superficial corneal tissue, and repositioning the corneal tissue in a rotated or inverted fashion thereby reducing visual impairment of the eye.

For example, the present invention may include the step of excising a cap of corneal tissue that has a desired size and/or shape based upon the desired vision improvement to be achieved. In some embodiments of the present invention, the corneal cap is similar in size and/or shape to a corneal flap formed in a conventional lasik procedure. Unlike a "lasik flap" however, the cap or disc of tissue excised in accordance with the present invention does not remain attached by a hinge. In addition, in accordance with some embodiments of the present invention, the corneal cap has a non-uniform thickness and/or shape. The position, size, orientation, and thickness of this disc is selected based upon the patient's refractive error and/or degree of astigmatism, such that when the cap is repositioned onto the eye, the repositioned cap will provide enhanced or improved vision, for example, by at least reducing the patient's refractive error.

More specifically, in accordance with one embodiment of the present invention, the step of removing tissue comprises freely excising a thin disc of tissue, hereinafter sometimes referred to as "disc of tissue" or "corneal cap" from the eye, and exposing the underlying corneal "bed" of stromal tissue.

Correcting vision with the methods of the present invention may be accomplished by any suitable means effective to enable the creation of a corneal disc of precise dimensions and location. For example, this could be accomplished with a femtosecond laser, which is in common use for the creation of lasik flaps and other corneal surgery. A microkeratome could also be fashioned with a blade that permits a variable flap thickness. These and other techniques and equipment suitable for creating precision cuts of an eye are well known in the art and therefore will not be described in great detail herein.

In embodiments of the invention directed at treating regular astigmatism, the disc of tissue, or corneal cap, may be excised with such precision so as to define a disc of tissue having a thickest region near or at a center of the tissue, and a relatively thinner region at the edges of the disc of tissue.

Turning now to FIG. 1, a simplified representation of a surface of an eye having regular astigmatism is shown in diagrammatical form. Most people with astigmatism have regular astigmatism. This usually occurs when the cornea has an oval (or toric) rather than a round curvature. In other words, one dimension of the cornea is steep and one dimension is flat.

Figure 2:
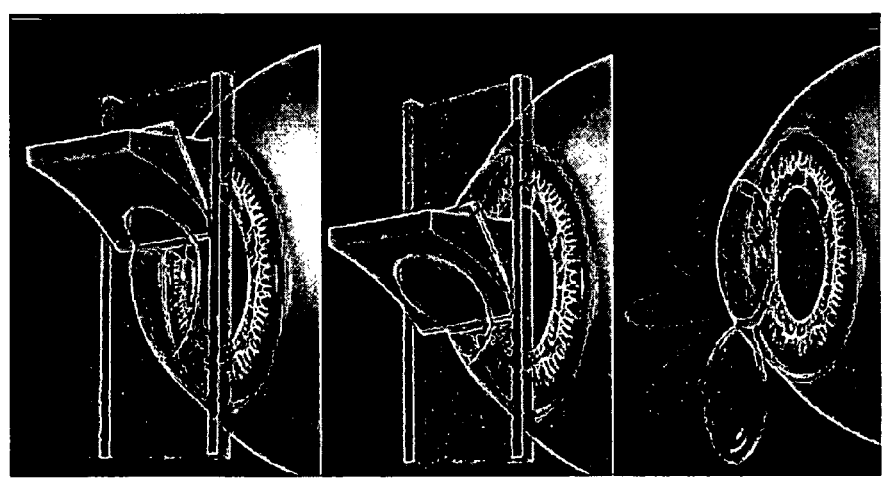
FIG. 2 shows a prior art procedure such as lasik, for correcting regular astigmatism wherein a thin hinged "flap" of corneal tissue is separated from the surface of the cornea and the underlying bed is reshaped with laser.

As shown in FIG. 2, in a prior art procedure such as lasik, for correcting regular astigmatism, a thin (e.g. 130 micron to 160 micron) hinged "flap" of corneal tissue is separated from the surface of the cornea. The exposed layers are then treated with a laser, for example using a laser to ablate portions of the exposed tissue, to achieve a desired curvature. The flap is then replaced on the laser treated tissue and allowed to heal.

Unlike such prior art procedures, in accordance with the present invention, a piece of corneal tissue is removed from the surface of the eye and is then repositioned on the corneal bed and allowed to heal in the new position. Laser treatment of underlying layers is not required or necessary to achieve the desired improvement or correction in vision. Thus, the structure and/or strength of the cornea is not compromised in any substantial manner by the present inventive procedures, relative to, for example, procedures which reshape the cornea by lasing portions of the underlying stromal bed to achieve vision correction.

Figure 3:
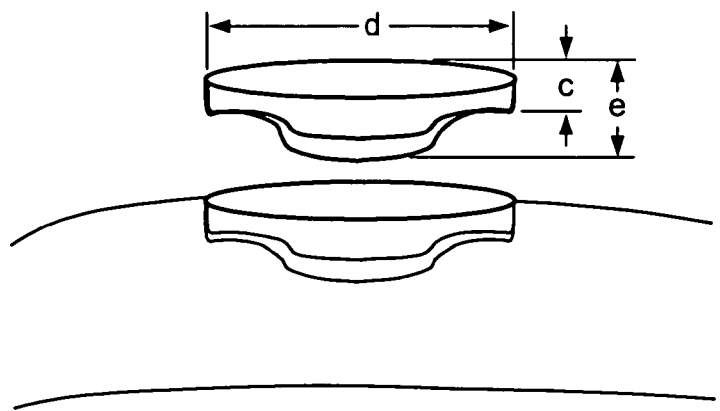
FIG. 3 shows a simplified representation of a corneal cap that has been removed during a procedure to improve or correct vision in accordance with the present invention.

Turning now to FIG. 3, in accordance with the present invention, in order to improve or correct vision of an eye having regular astigmatism, the corneal cap may be excised from the cornea such that the excised cap is similar, for example in size and shape, to a "plus cylinder" lens.

It is to be appreciated that in other embodiments of the present invention, the corneal cap may be excised such that it has a thinner central portion relative to the edges thereof, such as in a "minus cylinder" lens. In yet other embodiments of the present invention, for example cases of irregular astigmatism, the excised disc of tissue may have non-symmetrical thicker or thinner portions.

Figure 4:
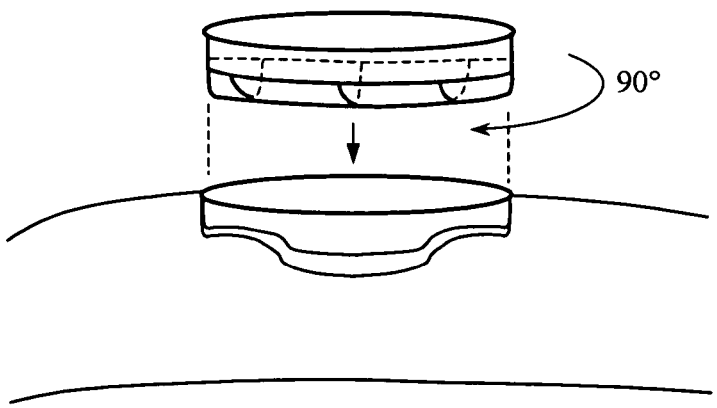
FIG. 4 shows a simplified representation of the corneal cap shown in FIG. 3, the corneal cap having been rotated during the procedure to improve or correct vision in accordance with the present invention.
Figure 5:
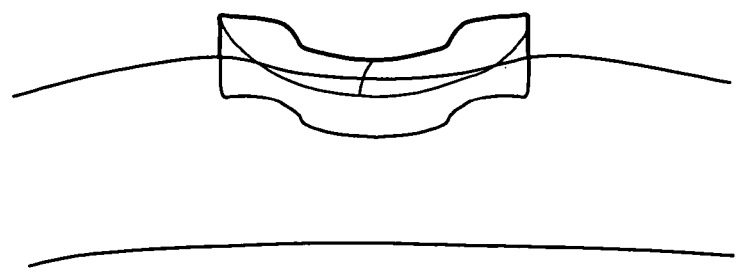
FIG. 5 shows a simplified representation of the corneal cap shown in FIG. 3, the corneal cap having been repositioned on the eye after the rotation shown in FIG. 4, during the procedure to improve or correct vision in accordance with the present invention.

The step of repositioning the corneal cap may comprise repositioning the tissue on the eye such that the tissue is placed at a selected degree of rotation relative to its original, pre-excised position. For example, as shown in FIG. 4, the corneal cap may be rotated to approximately 90 degrees from its natural or original position and then is replaced on the exposed stromal bed, and allowed to heal in the rotated position. As shown in FIG. 5, after healing, the corneal surface of the eye in this particular example, has a flatter meridian 90 degrees away from a steeper meridian, similar to an optical Jackson Cross Cylinder.

It is to be appreciated that the repositioning step may include inverting the corneal cap and placing the inverted corneal cap onto the eye. Also, in some cases, the corneal cap may be modified (e.g., reshaped, lased, excised, partially removed or ablated, etc) before it is repositioned on the eye to facilitate the desired vision correction.

Generally, for correcting astigmatism, the disc of tissue will typically have dimensions at least in part based on the patient's astigmatic variables. For cases of irregular astigmatism, astigmatic variables can be determined by procedures known in the art and therefore will not be described in great detail herein.

In accordance with some embodiments of the present invention, the surgical technique involves marking the cornea's surface with dye. Radial markings on the cornea may be placed with an instrument such as a radial keratotomy (RK) marker. For example, if these marks are 90 degrees apart (as they are in a 4 incision RK marker), the corneal cap may be rotated by 90 degrees with a fairly high degree of precision. Other angles of rotation may be similarly achieved with RK markers having a different number of radial marks.

A femtosecond laser or microkeratome device may be programmed for the desired flap shape and a flap is created. In accordance with the present invention, the surgeon then frees the flap creating a corneal cap. The excised corneal cap is then rotated to a desired degree, which is typically determined pre-operatively and is dependent, at least in part, on the patient's visual aberration to be improved or corrected. The rotated corneal cap is then allowed it to settle on the corneal bed in its new position. Postoperative care may be substantially or identically similar to the standard of postoperative care in a conventional lasik procedure, which generally includes protecting the eye from trauma and administering anti-inflammatory and antibiotic eye drops.

Although the present invention is described herein to generally be directed at utilizing laser equipment in the methods of the present invention, the scope of the present invention is not considered to be limited thereto. For example, other means of precision cutting may be employed that are suitable for facilitating the removal of a corneal cap having a desired geometry in order to achieve a desired vision improvement or vision correction.

For purposes of example only, not to be considered limiting the scope of the invention, the following formula may be used to calculate dimensions of a corneal cap when rotation of 90 degrees is used in order to improve or correct vision. Of course, it is to be appreciated that appropriate modifications may be made as necessary or desirable to achieve a desired result, and such modifications are considered to be included within the scope of the invention.

Munnerlyn Formula: depth≈diam2×diopters/3

Modified: $e-c \approx d2 \times diop\ cyl/6$

Rearranging: diop cyl≈3×(e−c)/d2 total correc≈6×(e−c)/d2 where:
"diop cyl" represents the astigmatic correction (in diopters);

"e" represents the thickest dimension of the corneal cap (in microns);

"c" represents the thinnest dimension of the corneal cap (in microns); and

"d" represents the diameter of the cap (in mm).

Figure 9:
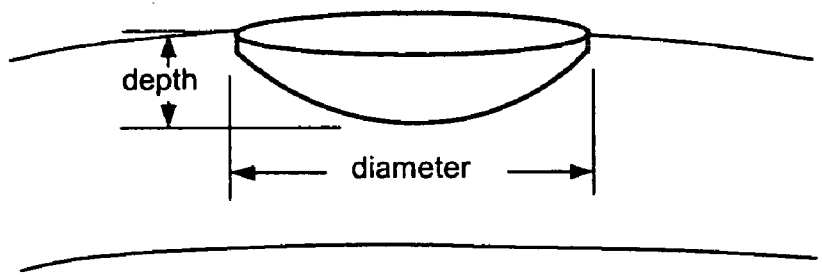
FIGS. 9-11 are schematic diagrams illustrating the application of formulas in accordance with the present invention.
Figures 10, 11:
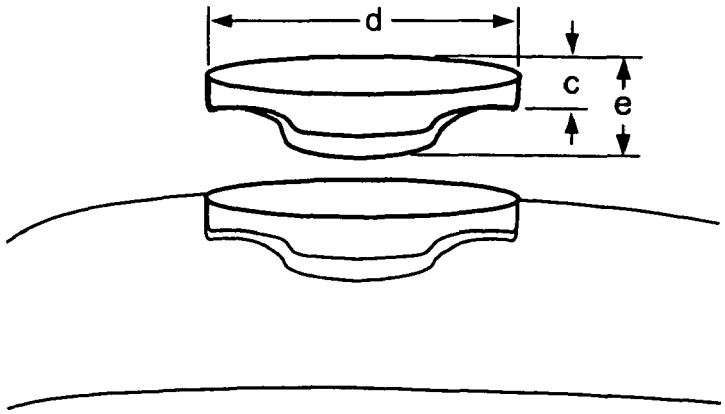

Those of skill in the art will further appreciate these calculations and the basis therefore from the showings of FIGS. 9-11.

Example 1

This method may be modified to treat irregular astigmatism or higher order aberrations as well conventional forms of refractive error. Unlike the specific example above, the disc could be fashioned with a non-symmetrical shape with respect to its positioning, shape, thickness, or rotation.

Figure 6:
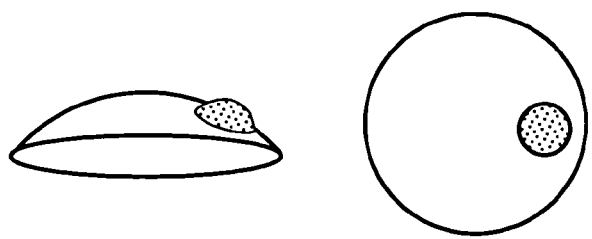
FIG. 6a shows a simplified diagram of an irregular cornea with a thickened area (shaded region) on one side that creates irregular astigmatism.
FIG. 6b shows a simplified diagram of the irregular cornea shown in FIG. 6a after a disc of corneal tissue has been repositioned in accordance with an embodiment of the present invention, resulting in thickened areas that are less steep (shaded areas) and, thus, improved vision.
Figure 6:
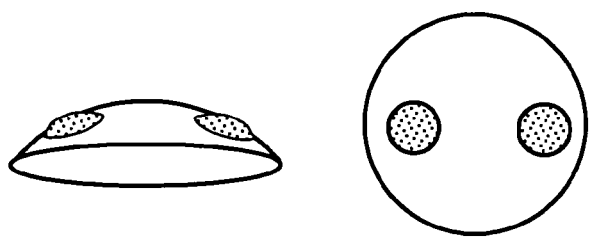

For example, in the case of a patient with a thickened corneal scar on one side of the cornea, the disc might have a uniform thickness everywhere except in the area underlying the scar, where it would be thicker (the cornea cut deeper below the surface) by an amount roughly equal to half the thickness of the scar itself. This disc would be lifted and rotated, for example, about 180 degrees, before replacing it on the cornea (FIG. 6). This would have the effect of dividing the locally steepened area (the scar) represented by a single shaded area in FIG. 6A into two roughly equal steepened areas that are diametrically opposite on the cornea (represented by two separate shaded areas in FIG. 6A). These paired, symmetrical steepened areas would create an optical effect similar to regular astigmatism, which would allow simpler options for subsequent optical correction.

A similar method could be employed for treatment of visual distortion resulting from a decentered previous refractive laser treatment. Other corneal irregularities can also be treated in a similar fashion. In each case, the position, placement, shape, thickness, and rotation of the corneal disc would be dictated by the patient's own refractive error, including higher order aberrations. The goal would be to achieve a new corneal shape that would improve vision.

Example 2

A 43 year old female with a refraction of −5.00 sphere OD and −3.50 sphere OS and corrected visual acuity of 20/20 OU wished to have refractive surgery. Surgery in the left eye was uncomplicated and resulted in postoperative uncorrected vision of 20/20. Her lasik procedure in the right eye was complicated by a free cap unintentionally created by the Automated Corneal Shaper (Bausch and Lomb, Rochester, N.Y.). The surgeon then performed a spherical myopic ablation. At the completion of the ablation, the surgeon was unable to identify the inked orientation marks he had made on the corneal surface before the keratectomy. He replaced the flap in what he believed was the correct orientation. Postoperatively, her refraction was −0.50+3.00×062 correcting the eye to 20/30. A pinhole improved vision to 20/20. Topography showed bow-tie astigmatism (FIG. 1). The patient is left with residual astigmatism and reduction in BCVA.

Example 3

A patient (e.g., the patient of Example 2 above) presents with postoperative astigmatism that has been caused by unintentional rotation of a free lasik cap before replacing it.

Figure 7:
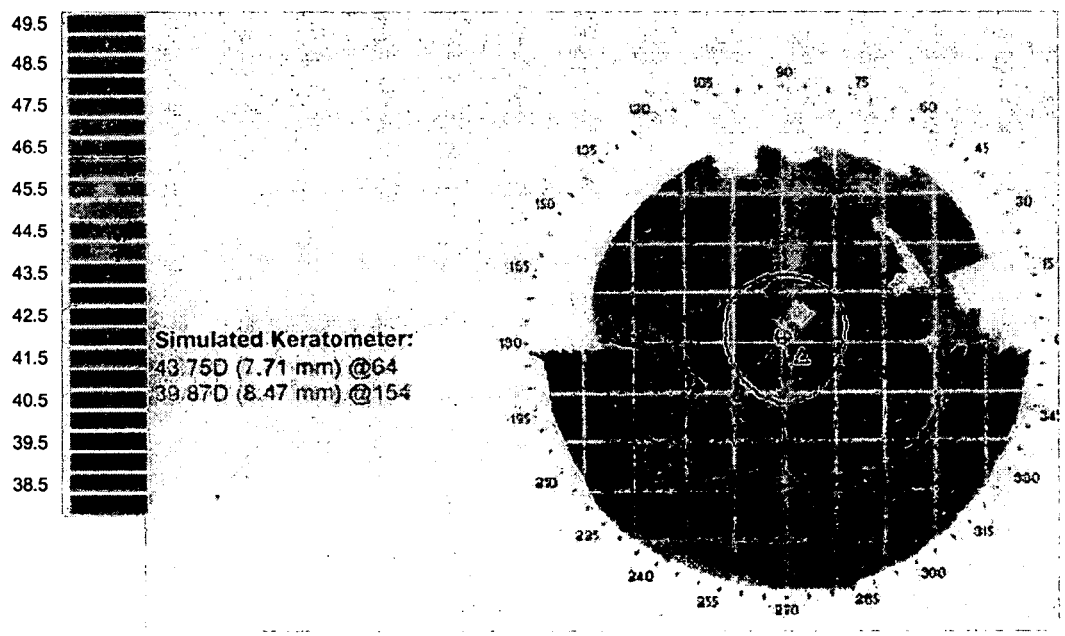
FIG. 7 shows topography of a cornea prior to performance of a procedure to correct vision in accordance with an embodiment of the present invention.

The preoperative topography of the patient's eye was measured and is shown in FIG. 7. After a thorough examination of the patient's eye, it is hypothesized that during a keratotomy procedure, a microkeratome had been passed through stromal tissue such as to create a cut that was shallow at the beginning and end of the cut but of relatively normal depth in the center. The "free cap" was therefore shaped like a plus power cylindrical lens with axis at 90° and power at 180°. The stromal bed had similarly been deeper centrally and shallower at the ends where the blade entered and exited the cornea. The stromal bed had the shape of a minus cylinder with power at 180°.

It is noted that had the cap been replaced in its original configuration, the deep and shallow areas would have matched, i.e. the plus and minus cylinders would have canceled each other, and there would have been little or no net effect of the keratotomy on corneal astigmatism. However, in this case, the cap had been unintentionally rotated before it was replaced, and therefore the net effect on corneal astigmatism that resulted was the sum of the plus and minus power cylinders combined at an oblique axis to each other.

In accordance with the present invention, the angle of cap rotation is determined using the application of principles of optics. For example, it is assumed that the stromal cap is a plus cylinder rotated counterclockwise so its power is now at angle $\theta$, and the stromal bed is a minus cylinder with power at axis 0° the original axis of the temporal microkeratome cut.

Figure 8:
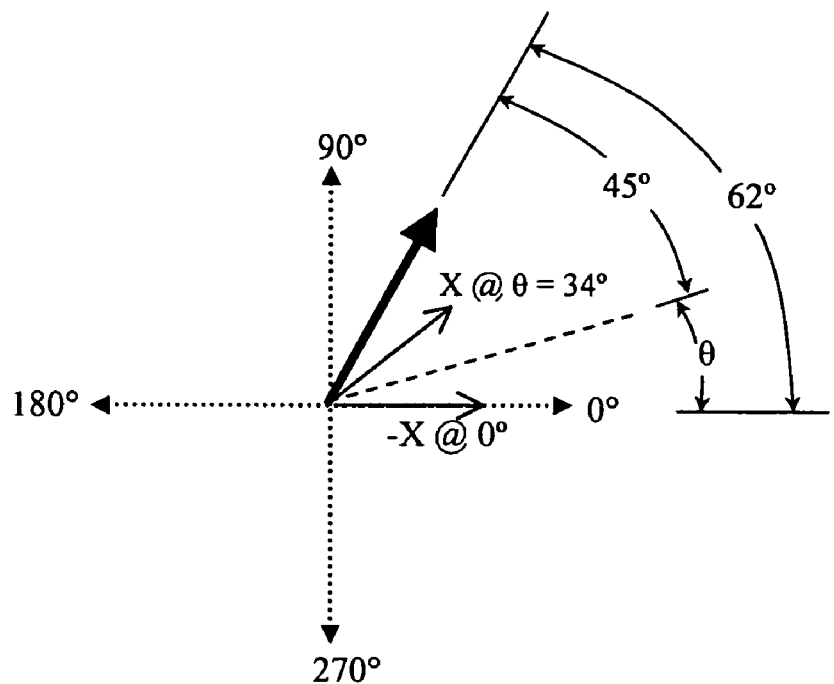
FIG. 8 shows a mathematical analysis of the angle of rotation of a free cap of corneal tissue.

According to Rubin, M L., *Optics for Clinicians*, Triad Scientific Publishers, 1971, 179-181, the optical effect of these two lenses can be described by a single spherocylinder whose power axis is 45° away from the bisector of the angle $\theta$. This is illustrated in FIG. 8. By refraction, the patient's cornea has its power axis at 62°. The bisector of the angle $\theta$ between the cap and the stromal bed must be 45° away from the refractive astigmatism, which is 17°. The bisector of angle $\theta$ is 45°. Hence, the cap had been rotated 34° counterclockwise when the surgeon replaced it.

Generally, it is assumed that the free cap is a plus cylinder of unknown magnitude X rotated counterclockwise so its power is now at angle $\theta$, while the bed of the keratectomy is a minus cylinder of equal magnitude with power at 0°. It is noted that determining the degree of rotation does not require knowledge of X, the magnitude of the astigmatism.

This patient is treated in accordance with the present invention by lifting the corneal cap, rotating it 34° clockwise, and replacing it. To ensure a rotation of as close to 34° as possible, the cornea is marked with a six incision RK marker prior to lifting the cap. Because each mark is 60° apart, the cap is rotated clockwise just far enough to make the marks on the cap fall in between those on the remaining cornea.

Three months after this cap rotation, the patient's uncorrected visual acuity improved to 20/30 and her refraction is −1.00+0.50×038, yielding 20/15 vision. The topography of the patient's cornea was again measured after 34° counterclockwise rotation of free cap and showed significantly less corneal astigmatism.

The invention has been described herein with reference to certain examples and embodiments only. No effort has been made to exhaustively describe all possible examples and embodiments of the invention. Indeed, those of skill in the art will appreciate that various additions, deletions, modifications and other changes may be made to the above-described examples and embodiments, without departing from the intended spirit and scope of the invention as recited in the following claims. For example, where the steps of a method are described or claimed in a particular order, the order of some or all of those steps may be changed unless doing so would render the method unsuitable for its intended purpose or no longer novel over the prior art. It is intended that all such additions, deletions, modifications and other changes be included within the scope of the following claims.

What is claimed is:

1. A method for correcting refractive error in an eye of a human or animal subject, the method comprising the steps of:
    A) determining the refractive error;
    B) measuring topography of the cornea of the eye;
    C) marking the cornea to indicate the existing rotational orientation of a corneal tissue cap;
    D) excising the corneal tissue cap from the eye in a manner that causes either i) a center portion of the cap to be thicker than the edges surrounding that center portion or ii) a center portion of the cap to be thinner than the edges surrounding that center portion;
    E) determining, based on the measured refractive error and corneal topography as well as the configuration of the excised corneal tissue cap, an adjusted rotational orientation in which the excised corneal tissue cap may be repositioned on the eye in order to correct the refractive error;
    F) repositioning the excised corneal tissue cap on the eye in the adjusted rotational orientation determined in Step E to thereby correct the refractive error.

2. A method according to claim 1 wherein the refractive error is due, at least in part, to astigmatism.

3. A method according to claim 1 wherein excising of the corneal tissue cap in Step D is performed using a laser or blade microkeratome.

4. A method according to claim 1, wherein the method is carried out without laser treatment of the non-excised corneal tissue.

* * * * *